United States Patent [19]

Cabrera et al.

[11] Patent Number: 5,614,626
[45] Date of Patent: Mar. 25, 1997

[54] 1,2,3-OXATHIAZIN-4(3F)-ONE 2,2-DIOXIDES, A PROCESS FOR THEIR PREPARATION AND THEIR USE AS ELECTROPHILIC FLUORINATING AGENTS

[75] Inventors: Ivan Cabrera, Dreieichenhain; Wolfgang Appel, Kelkheim, both of Germany

[73] Assignee: Hoechst AG, Germany

[21] Appl. No.: 500,166

[22] Filed: Jul. 11, 1995

[30] Foreign Application Priority Data

Jul. 13, 1994 [DE] Germany .................. 44 25 407.5

[51] Int. Cl.$^6$ .................................................. C07D 291/06
[52] U.S. Cl. ............................................................. 544/2
[58] Field of Search ................................................ 544/2

[56] References Cited

U.S. PATENT DOCUMENTS

| | | | |
|---|---|---|---|
| 4,479,901 | 10/1984 | Barnette | 260/239 |
| 4,828,764 | 5/1989 | DesMarteau | 260/397 |
| 5,086,178 | 2/1992 | Banks | 544/351 |
| 5,227,493 | 7/1993 | Banks | 546/307 |

FOREIGN PATENT DOCUMENTS

| | | |
|---|---|---|
| 0211578 | 2/1987 | European Pat. Off. . |
| 3623184 | 1/1988 | Germany . |

OTHER PUBLICATIONS

Purrington, S. T., et al, *J. Org. Chem.* 48:761–762 (1983).
Banks, R. E., et al, *J. Chem. Soc. Perkin Trans. I:* 2805–2811 (1988).
Differding E., et al, *Tetrahedron Letters* 29:6087–6090 (1988).
Umemoto, T., et al, *J. Am. Chem. Soc.* 112:8563–8575 (1990).
Tetrahedron, Bd. 47, Nr. 35, Aug. 26, 1991, Oxford GB, pp. 7447–7458, *N–Fluorination with Cesium fluoroxysulfate.*
Cram and Hammond, "Organic Chemistry", 2nd Edition, pp. 565–567 (1964).

*Primary Examiner*—John M. Ford
*Attorney, Agent, or Firm*—Connolly & Hutz

[57] ABSTRACT

The invention relates to compounds of the formula (I)

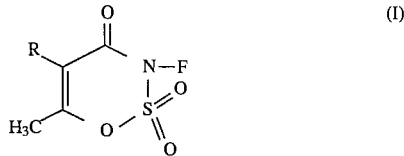

which R is hydrogen or $(C_1–C_4)$-alkyl, to a process for their preparation and to their use as electrophilic fluorinating agents.

2 Claims, No Drawings

1,2,3-OXATHIAZIN-4(3F)-ONE 2,2-DIOXIDES, A PROCESS FOR THEIR PREPARATION AND THEIR USE AS ELECTROPHILIC FLUORINATING AGENTS

The invention relates to 1,2,3-oxathiazin-4(3F)-one 2,2-dioxides, to a process for their preparation and to their use as electrophilic fluorinating agents.

Many new agricultural and pharmaceutical active substances contain F atoms at strategic positions. One reason for this is the fact that the replacement of hydrogen by fluorine (isosteric substitution) or of hydroxyl groups by fluorine (isopolar substitution) very often leads to an improvement in their activity. The selective introduction of fluorine into organic molecules has therefore become a very important task in modern chemistry. Although the introduction of diethylaminosulfur trifluoride and other reagents in this class of compounds has represented a breakthrough in the field of nucleophilic fluorination, there continues to be a need for safe, mild and efficient electrophilic fluorinating agents. The majority of such electrophilic reagents, for example perchloryl fluoride, trifluoromethyl hypofluoride, $CsSO_4F$, etc., are toxic and very aggressive chemicals with which explosions have been observed in many cases. Furthermore, the stability of such materials on storage is very limited. "$F^{\oplus}$" reagents based on compounds containing N—F have undergone very detailed investigation, since some of these materials have proven to be readily isolable, storage-stable and efficient fluorinating agents. Initial experiments in this direction were carried out using perfluoro-N-fluoropiperidine (A) (J. Chem. Soc. Perkin Trans. I 1988, 2805). However, owing to the complex synthesis (maximum yield 13%) and the secondary reaction during the fluorination, this compound is of no interest for practical purposes. Other known N—F fluorinating agents are N-fluoropyridin-2-(1H)-one (B) (J. Org. Chem. 1983, 43, 761), N-fluorosulfonamides (C) (U.S. Pat. Nos. 4,479,901, 4,828,764, DE 36 23 184 A); camphor N-fluorosultam (D) (Tetrahedron Lett. 1988, 29, 6087); N-fluoroquinuclidinium salts (E) (J. Chem. Soc. Perkin Trans I, 1988, 2805); N-fluoropyridinium salts (F) (J. Am. Chem. Soc. 1990, 112, 8563); N-fluoro-N-perfluoromethyl sulfonamides (G) (U.S. Pat. No. 4,828,764, U.S. Pat. No. 5,227,493) and N-fluoro-N-chloromethyltriethylenediamine bis(tetrafluoroborate) (F-Teda (H)) (U.S. Pat. No. 5,086,178).

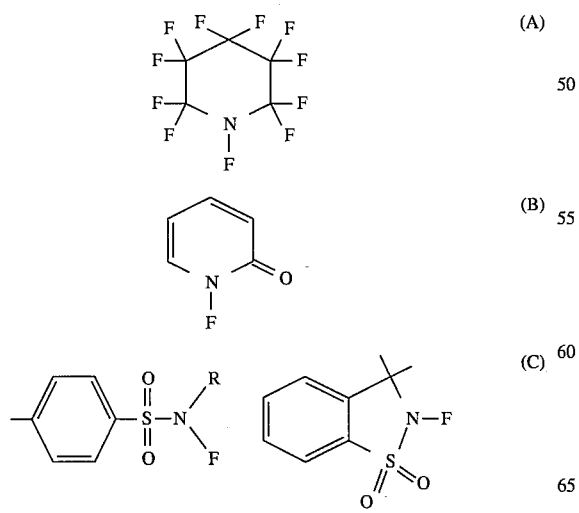

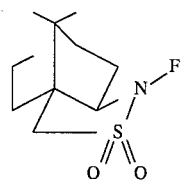

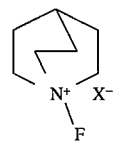

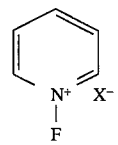

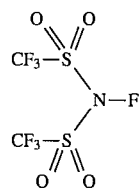

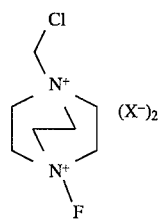

Compound (B) is not stable on storage. The reagent (G), which is the strongest known NF compound, requires a very complex synthesis for its preparation. Compounds (C), (F) and (H) are commercially available. The commercial N-fluorosulfonamides, however, have the disadvantage that, because of the hydrogen atom at the α position of the N-alkyl radical, elimination of HF can very easily take place as a secondary reaction. With N-alkyl radicals which do not possess hydrogen atoms in the α position, for example a t-butyl group, the yield in the preparation of the NF compound is very low. Although the charged systems (H) and (F) are highly efficient fluorinating agents, a decisive disadvantage of these systems is their limited solubility in the usual organic solvents. F-Teda (H) has the additional disadvantage that a Hofmann elimination often takes place with this quaternary ammonium salt. This is a particular problem in the fluorination of strong carbanions.

There was therefore a great need for an electrophilic fluorinating agent which does not have the disadvantages described, which can be easily prepared from readily available starting materials and which possesses good stability on storage.

This object is achieved by compounds of the formula (I)

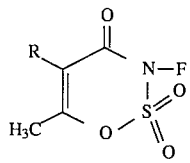

(I)

in which R is hydrogen or $(C_1-C_4)$-alkyl.

Advantageous compounds of the formula (I) are those in which R is hydrogen or methyl.

Depending on the solvent, it is also possible for the compounds of the formula (I) to be in tautomeric equilibrium with the compounds of the formula (I'):

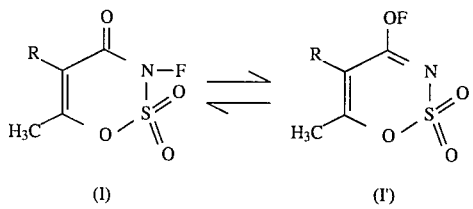

(I)            (I')

The invention additionally provides a process for the preparation of the compounds of the formula (I). This process comprises reacting compounds of the formula (II) in which R is as defined above and X is hydrogen or an alkali metal with elemental fluorine in the presence of an inert solvent and, if desired, of an alkali metal fluoride at low temperatures.

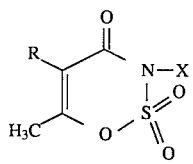

(II)

The compounds (II) are products of large-scale industrial processes (R=H) or can be prepared in a manner known from the literature.

Good results are obtained, for example, if X is hydrogen, sodium or potassium.

Highly suitable alkali metal fluorides are sodium fluoride or potassium fluoride, especially sodium fluoride.

The fluorinating agent, fluorine, is advantageously employed in a mixture with inert gases such as nitrogen, $SF_6$ or $CF_4$ or noble gases such as helium, neon, argon or krypton. The preferred inert gas is nitrogen. For the fluorination it is possible to employ fluorine/inert gas mixtures containing up to 30% by volume of fluorine.

In many cases it has been found appropriate to carry out the fluorination using an $N_2/F_2$ mixture which contains between 1 and 15% by volume, in particular between 2 and 10% by volume, preferably from 3 to 6% by volume, of $F_2$.

Examples of suitable solvents are halogenated hydrocarbons such as dichloromethane, chloroform, carbon tetrachloride, fluorotrichloromethane, trifluorotrichloroethane or tetrafluorodichloroethane, or nitriles, especially acetonitrile.

The temperature at which the reaction is carried out can be varied within a wide range and is, in particular, in the range from +10° to −80° C. The choice of temperature in each individual case depends on the chosen reaction conditions, such as the concentration of fluorine, composition of the solvent mixture, etc. The fluorination is carried out advantageously at temperatures of from −80° to −20° C., in particular from −60 to −30° C. and preferably from −50° to −35° C.

The invention additionally provides for the use of the compounds of the formula (I) for the fluorination of compounds possessing an open or concealed carbanion character, for example 1,3-dicarbonyl compounds. These compounds can be reacted in very high yields to give the fluorine compounds.

The compounds of the formula (I) are capable of producing iodine when treated with sodium iodide solution. The concentration of the compounds can therefore be determined by means of titration.

EXAMPLE 1

5,6-Dimethyl-1,2,3-oxathiazin-4(3F)-one 2,2-dioxide

In a completely dry (flame-treated) fluorination apparatus under $N_2$, 0.22 g of NaF (5.4 mmol) is added to a suspension of 1.08 g (5.4 mmol) of 5,6-dimethyl-1,2,3-oxathiazin-4(3H)-one 2,2-dioxide, sodium salt, in 120 ml of $CaH_2$-dried acetonitrile (Chromasolv R for HPLC) and the mixture is fluorinated at −40° C. using a mixture of 5% (v/v) $F_2$ in $N_2$. Flushing with $N_2$ is then carried out at −40° C. for 0.5 h and at room temperature for 1 h. The mixture is filtered and the filtrate is rapidly distilled under an oil pump vacuum. The yellow oil is taken up in dried ether, clarified by filtration and concentrated on a rotary evaporator. Drying under an oil pump vacuum gives 0.55 g of product (pale yellow oil).

$^1$H-NMR (300 MHz, $CDCl_3$): δ(ppm) 2.02 (quintet, $CH_3$—C—CO); 2.30 (quartet, $CH_3$—C—O). $^{19}$F-NMR (94.2 MHz, $CH_3CN$): δ(ppm, standard $CFCl_3$) −78 (b, NF).

EXAMPLE 2

6-Methyl-1,2,3-oxathiazin-4(3F)-one 2,2-dioxide

Fluorination as described above of a mixture of 1.38 g of acesulfame (6-methyl-1,2,3-oxathiazin-4(3H)-one 2,2-dioxide) and 1.78 g of NaF in 120 ml of acetonitrile gave 0.92 g of a yellow oil.

$^1$H-NMR (100 MHz, $CDCl_3$): δ(ppm) 2.18 (d, $CH_3$-); 5.81 (m, 1H). $^{19}$F-NMR (94.2 MHz, $CH_3CN$): δ(ppm, standard $CFCl_3$): −78.8 (b, NF).

The Examples which follow are intended to illustrate the use of the oils described above:

EXAMPLE 3

Ethyl 2-fluorocyclopentanone-2-carboxylate

A solution of 207 mg (1.3 mmol) of ethyl cyclopentanone-2-carboxylate in 60 ml of dried THF was added at 0° C. under Ar to a suspension of 42 mg of NaH (80% in oil/10 ml of THF). The mixture was stirred at 0° C. for 0.5 h and at room temperature for 1 h, after which the oil of Example 2 (0.5 g) was added. The reaction mixture was stirred at room temperature for 4 h. The solvent was stripped off on a rotary evaporator. The residue was taken up in ether and clarified by filtration and the filtrate was subjected to extraction by shaking with water, saturated $NaHCO_3$ solution and water. The ether phase was then dried over $Na_2SO_4$ and filtered and the solvent was removed in vacuo. Yield: 152 mg (67% of theory).

EXAMPLE 4

Diethyl 2-fluoro-2-phenylmalonate

A solution of 284 mg (1.2 mmol) of diethyl 2-phenylmalonate in 50 ml of dried THF was added at 0° C. under Ar to a suspension of 36 mg of NaH (80% in oil/10 ml of THF). The mixture was stirred at 0° C. for 0.5 h and at room temperature for 1 h, after which the oil of Example 1 (0.3 g) was added. The reaction mixture was stirred at room temperature for 4 h. The solvent was stripped off on a rotary evaporator. The residue was taken up in ether and clarified by filtration and the filtrate was subjected to extraction by shaking with water, saturated $NaHCO_3$ solution and water. The ether phase was then dried over $Na_2SO_4$ and filtered and the solvent was removed in vacuo. Yield: 250 mg (82% of theory).

We claim:

1. A compound of the formula (I)

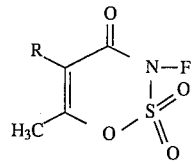

in which R is hydrogen or $(C_1-C_4)$-alkyl.

2. A compound of the formula (I) in which R is hydrogen or methyl.

* * * * *